United States Patent
Yamashita et al.

(10) Patent No.: US 9,981,070 B2
(45) Date of Patent: May 29, 2018

(54) COATING COMPOSITION AND MEDICAL DEVICE

(71) Applicant: TERUMO KABUSHIKI KAISHA, Shibuya-ku, Tokyo (JP)

(72) Inventors: Keiko Yamashita, Kanagawa (JP); Shigenori Nozawa, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 224 days.

(21) Appl. No.: 14/859,913

(22) Filed: Sep. 21, 2015

(65) Prior Publication Data

US 2016/0015864 A1 Jan. 21, 2016

Related U.S. Application Data

(63) Continuation of application No. PCT/JP2014/059670, filed on Apr. 1, 2014.

(30) Foreign Application Priority Data

Apr. 1, 2013 (JP) .................................. 2013-076387

(51) Int. Cl.
*A61K 9/00* (2006.01)
*A61L 29/16* (2006.01)
*A61L 29/08* (2006.01)
*A61L 31/08* (2006.01)
*A61L 31/16* (2006.01)
*A61K 31/337* (2006.01)
(Continued)

(52) U.S. Cl.
CPC ............ *A61L 29/16* (2013.01); *A61K 31/337* (2013.01); *A61K 31/436* (2013.01); *A61L 29/08* (2013.01); *A61L 31/08* (2013.01); *A61L 31/16* (2013.01); *A61M 25/10* (2013.01); *A61L 2300/416* (2013.01); *A61L 2300/606* (2013.01); *A61L 2420/06* (2013.01); *A61M 2025/105* (2013.01)

(58) Field of Classification Search
CPC ....................................................... A61L 29/16
See application file for complete search history.

(56) References Cited

U.S. PATENT DOCUMENTS 5,417,981 A 5/1995 Endo et al.
6,228,391 B1 5/2001 Shimizu et al.
(Continued)

FOREIGN PATENT DOCUMENTS

JP 6-023032 A 2/1994
JP 9-075446 A 3/1997
(Continued)

OTHER PUBLICATIONS

Machine translation of WO1997042166 to Knuerr, Jun. 24, 2017.*
(Continued)

*Primary Examiner* — Paul W Dickinson
(74) *Attorney, Agent, or Firm* — Buchanan, Ingersoll & Rooney PC

(57) ABSTRACT

A coating composition capable of forming a drug coating layer insusceptible to peeling in the process of delivery of a water-insoluble drug to a target tissue is provided. The coating composition contains the water-insoluble drug and a basic compound which is positively charged at physiological pH. A medical device coated with the coating composition is further provided.

8 Claims, 4 Drawing Sheets

(51) Int. Cl.
*A61M 25/10* (2013.01)
*A61K 31/436* (2006.01)

(56) References Cited

U.S. PATENT DOCUMENTS

| | | | | |
|---|---|---|---|---|
| 6,232,336 | B1* | 5/2001 | Hrabie | C07C 251/08 514/401 |
| 7,438,925 | B2* | 10/2008 | Hsu | A61K 31/4745 424/400 |
| 2003/0216806 | A1* | 11/2003 | Togawa | A61F 2/91 623/1.15 |
| 2005/0209664 | A1 | 9/2005 | Hunter et al. | |
| 2010/0209472 | A1 | 8/2010 | Wang | |
| 2012/0046756 | A1* | 2/2012 | Wang | A61F 2/82 623/23.7 |
| 2013/0224255 | A1* | 8/2013 | Hossainy | A61F 2/82 424/400 |

FOREIGN PATENT DOCUMENTS

| | | |
|---|---|---|
| JP | 2010-540159 A | 12/2010 |
| WO | WO 97/42166 A1 | 11/1997 |
| WO | WO 97/47166 A1 | 12/1997 |
| WO | WO 2007/041584 A2 | 4/2007 |
| WO | WO 2009/051614 A1 | 4/2009 |
| WO | WO 2011/119159 A1 | 9/2011 |

OTHER PUBLICATIONS

International Search Report (PCT/ISA/210) dated Jul. 8, 2014, by the Japanese Patent Office as the International Searching Authority for International Application No. PCT/JP2014/059670.
Search Report issued by the European Patent Office dated Sep. 13, 2017 in corresponding European Patent Application No. 14 780 002.3-1455 (6 pages).

* cited by examiner

COATING COMPOSITION AND MEDICAL DEVICE

CROSS-REFERENCES TO RELATED APPLICATIONS

This application is a continuation of International Application No. PCT/JP2014/059670 filed on Apr. 1, 2014, designating the U.S. and claims priority to Japanese Application No. 2013-076387 filed on Apr. 1, 2013, the entire content of which is incorporated herein by reference.

TECHNICAL FIELD

Disclosed is a coating composition for a drug eluting medical device, a drug coating layer for a drug eluting medical device, or a drug eluting medical device coated with the coating composition.

BACKGROUND DISCUSSION

As an example of local drug delivery therapy, there has been a drug eluting stent (DES). The DES is designed so as to release a drug locally and sustainedly for a long period of time, thereby preventing restenosis of a blood vessel. The sustained release of a drug from the DES is achieved by a polymer conjugate such as polylactic acid (PLA). However, since the polymer remains in the living body for a long period of time, there is a problem of severe complications such as chronic inflammation or delayed thrombosis in the lesion affected area.

In the past, it has been reported that sustained release of a drug for a long period of time is necessary for inhibiting restenosis. In recent years, however, it has been being made clear that by rapid transfer of a drug to a target tissue, even a short-term sustained drug release effect is sufficient for successfully preventing restenosis. The technology of rapid drug delivery does not need a polymer matrix, such as PLA or polylactic acid-glycolic acid copolymer (PLGA), for sustained release, and is therefore advantageous for avoiding complications.

Besides, in recent years, development of drug eluting balloons (Drug Eluting Balloon: DEB) wherein a balloon catheter is coated with a drug has been made positively, and it has been reported to be effective in treating and preventing restenosis. The balloon is coated with a coating layer that contains a drug and excipients, and, when a blood vessel is dilated, the balloon is pressed against the blood vessel wall so as to deliver the drug to the target tissue.

SUMMARY

If the drug easily peels off the balloon in the process of delivery of the balloon to a target tissue, however, the amount of the drug remaining on the balloon would be reduced to below a sufficient level for a therapeutic effect, before the balloon is delivered to the lesion affected area. In such a situation, the expected therapeutic effect cannot be desired. In addition, the drug easily peeled off during the delivery process is unnecessarily exposed into the blood, which is undesirable from the viewpoint of safety. Therefore, there is a need for a drug coating layer which ensures that a balloon catheter coated with a drug can be delivered to a lesion affected area without peeling of the drug, the balloon can be pressed against a blood vessel wall simultaneously with expansion, and the drug can thereby be released rapidly.

There has been a report that a hydrophilic drug can be delivered by use of a balloon catheter coated with a hydrogel of a hydrophilic polymer. On the other hand, a water-insoluble drug may, in some cases, be difficult to mix with a hydrophilic polymer that forms a hydrogel, so that it is difficult to deliver the drug effectively. If the mixing is achieved, the coating layer in which the hydrophilic polymer and the drug are mixed is poor in adhesion to a medical device, and it is considered that under the influence of the high polarity, the drug is easily eluted into blood rather than being delivered to a target tissue. Therefore, where a hydrophilic polymer is used, the coating layer is easily separated in the process of being delivered to a lesion affected area, and it is difficult to enhance the migration of the drug to the target tissue.

On the other hand, where a hydrophobic polymer so highly hydrophobic as not to be dissolved in water is used, the strong hydrophobic interaction between the hydrophobic polymer and the water-insoluble drug improves durability of the drug coating layer in the delivery process. However, at the same time, the strong interaction between the drug and the hydrophobic polymer makes it impossible to rapidly release the drug in a lesion affected area. In addition, molecules of the water-insoluble hydrophobic drug aggregate onto each other or onto the surface of the medical device, making it impossible to achieve uniform coating. Further, the aggregated state of the drug leads to easy separation (detachment) during handling, which is undesirable from the viewpoints of safety and function.

For this reason, for therapy of an affected area of blood vessel such as restenosis, there is a need for a coating layer for a medical device which enables a drug to be delivered to a target tissue without easily peeling from the medical device in the process of delivery to the target tissue, which enables the drug to be rapidly released in the lesion affected area after delivery, and which can enhance the migration of the drug to the target tissue.

Accordingly, it is an object to provide a coating composition for a drug eluting medical device that is capable of forming a drug coating layer unsusceptible to peeling in the process of delivery of a water-insoluble drug to a target tissue, and a medical device coated with the coating composition.

As a result of their extensive and intensive studies for solving the above-mentioned problems, it has been found that when a coating composition containing a water-insoluble drug and a basic compound which is positively charged at physiological pH is used, it is possible to form, on a surface of a medical device, a drug coating layer which is enhanced in migration of the drug to tissue in a lesion affected area while preventing peeling-off of the drug coating layer during the process of delivery to the target tissue.

The basic compound contained in the drug coating layer has both a hydrophobic moiety including an alkyl group and a cationic moiety configured to be positively charged. It is considered that the hydrophobic moiety enhances affinity for a water-insoluble drug and a medical device surface (e.g., a balloon surface), and, on the other hand, the cationic moiety enhances affinity for cell surfaces which are anionically charged, thereby promoting migration of the drug to tissue.

As a similar structure, a phospholipid may be mentioned. Due to the presence of the phosphate group, however, the phospholipid is neutral or negatively charged, and never strongly positively charged, at physiological pH. For this reason, it is considered that the basic compound contained in the drug coating layer of the disclosed embodiments is stronger than the phospholipid in specific affinity for cells.

Therefore, even if a combination of phospholipid and a water-insoluble drug can enhance affinity for the drug and a medical device surface, the combination of the basic compound and the water-insoluble drug contained in the drug coating layer of the disclosed embodiments can be expected to provide better migration of drug to tissue at a target tissue.

Thus, disclosed are the following illustrative aspects.

(1) A coating composition to be used for a drug-eluting medical device, the coating composition containing a water-insoluble drug and a basic compound which is positively charged at physiological pH.

(2) The coating composition as described in the above (1), wherein the basic compound is at least one selected from the group consisting of a basic compound having an amidino group, a basic compound having a piperidine ring, a basic compound having two or more amino groups in one molecule thereof, a quaternary ammonium cation, and salts thereof.

(3) The coating composition as described in the above (1) or (2), wherein the basic compound is at least one selected from the group consisting of compounds represented by the following general formula (I) and salts thereof:

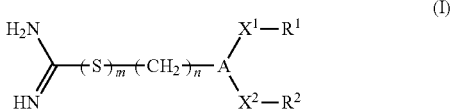

where A is an aromatic ring, $R^1$ and $R^2$ are each independently an alkyl or alkenyl group of 10 to 25 carbon atoms, $X^1$ and $X^2$ are each independently O, S, COO, OCO, CONH or NHCO, m is 0 or 1, and n is 0 or an integer of 1 to 6.

(4) The coating composition as described in any one of the above (1) to (3), wherein the basic compound is at least one selected from the group consisting of compounds represented by the following general formula (II) and salts thereof:

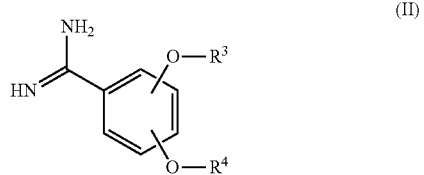

where $R^3$ and $R^4$ are each independently an alkyl group of 10 to 18 carbon atoms.

(5) The coating composition as described in any of the above (1) to (4), wherein the basic compound is at least one selected from the group consisting of compounds represented by the following general formula (III) and salts thereof:

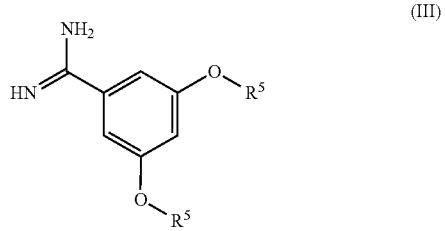

where $R^5$ are each independently an alkyl group of 10 to 18 carbon atoms.

(6) The coating composition as described in any one of the above (1) to (4), wherein the basic compound is at least one selected from the group consisting of compounds represented by the following general formula (IV) and salts thereof:

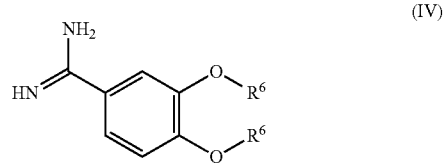

where $R^6$ are each independently an alkyl group of 10 to 18 carbon atoms.

(7) The coating composition as described in any one of the above (1) to (5), wherein the basic compound is 3,5-dipentadecyloxybenzamidine and/or a salt thereof.

(8) The coating composition as described in any one of the above (1) to (7), further containing a lower alcohol.

(9) The coating composition as described in the above (8), wherein the lower alcohol is glycerin.

(10) The coating composition as described in any one of the above (1) to (9), wherein the water-insoluble drug is at least one selected from the group consisting of rapamycin, paclitaxel, docetaxel, and everolimus.

(11) The coating composition as described in any one of the above (1) to (10), wherein the medical device is a medical device which can be expanded in a radial direction within a lumen.

(12) The coating composition as described in the above (11), wherein the medical device is a balloon or a catheter.

(13) A drug coating layer formed, by use of the coating composition as described in any one of the above (1) to (12), on at least part of a surface of the medical device.

(14) A medical device provided with the drug coating layer as described in the above (13).

(15) A treating method including: a step of delivering the medical device as described in the above (14) into a lumen; a step of radially expanding the medical device within the lumen; and a step of eluting a drug from the drug coating layer formed on at least part of the surface of the medical device and permitting the drug to act on the lumen.

According to the, it is possible to provide a coating composition for a drug eluting medical device, the coating composition being able to form a drug coating layer which is unsusceptible to peeling in the process of delivery to a target tissue and, on the other hand, can enhance migration of a drug to tissue at the target tissue.

When use is made of a drug eluting medical device having a drug coating layer formed of the disclosed coating composition, the drug can be efficiently delivered to a lesion affected area while inhibiting peeling of the drug coating layer. Moreover, in the lesion affected area, the drug can be rapidly released from the medical device capable of being radially expanded within a lumen, and the migration of drug to tissue can be enhanced by the cationic, basic compound coexisting with the drug.

DETAILED DESCRIPTION

1. Coating Composition

Figure 1:
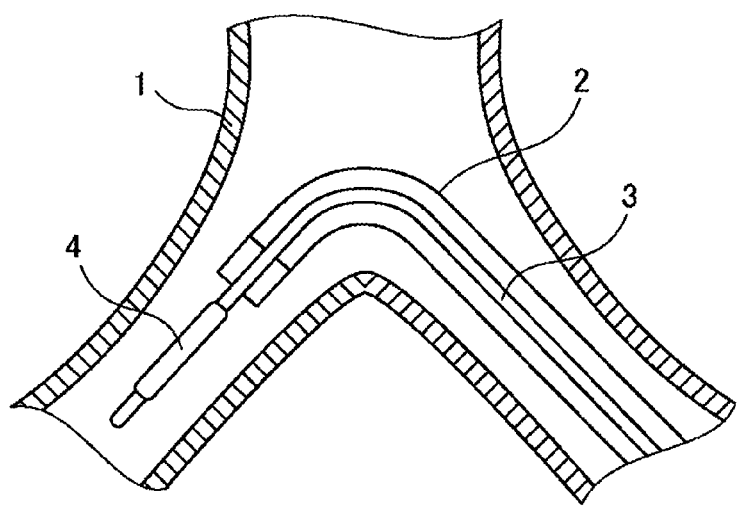
FIG. 1 is a sectional schematic view of an experimental apparatus in a state where a balloon catheter is inserted in a guiding catheter disposed in a mimic blood vessel, in a drug coating layer durability evaluation test using the mimic blood vessel.

The disclosed coating composition is a coating composition which contains a water-insoluble drug and a basic compound positively charged at physiological pH and which is to be used for a drug eluting medical device. Note that the disclosed coating composition is a mixture (blend) in which the water-insoluble drug and the basic compound positively charged at physiological pH are mixed (blended) with each other.

Since the disclosed coating composition contains the basic compound which is positively charged at physiological pH, affinity between the coating composition and a surface of a medical device is strengthened, so that a coating layer unsusceptible to peeling can be formed on the surface of the medical device. In addition, since the hydrophilicity of the coating layer is augmented, migration of drug to tissue is enhanced.

(1) Water-insoluble Drug

The water-insoluble drug refers to a drug which is insoluble or difficulty soluble in water, specifically having a solubility in water of less than 5 mg/mL at pH 5 to 8. The solubility may be less than 1 mg/mL, or even less than 0.1 mg/mL. The water-insoluble drug includes fat-soluble drugs.

Some preferred exemplary water-insoluble drugs include immunosuppressants, for example, immunologically active agents such as cyclosporines (including cyclosporine), rapamycin, etc., carcinostatic agents such as paclitaxel, etc., antiviral or antibacterial agents, antineoplastic agents, analgesic and anti-inflammatory agents, antibiotic, antiepileptic, anxiolytic agents, antiparalytic, antagonists, neuron blocking agents, anticholinergic and cholinergic agents, muscarine antagonists and muscarine agents, antiadrenergic agents, antiarrhythmic agents, antihypertensive agents, hormone preparations, and nutritional supplements.

The water-insoluble drug is preferably at least one selected from the group consisting of rapamycin, paclitaxel, docetaxel and everolimus. Rapamycin, paclitaxel, docetaxel and everolimus include their analogs and/or their derivatives so long as the analogs and/or derivatives have the same or equivalent efficacy to the original. For instance, paclitaxel and docetaxel are in the relation of analogs, whereas rapamycin and everolimus are in the relation of derivatives. Among these, more preferred is paclitaxel.

The content of the water-insoluble drug in the coating composition is not particularly limited, but the concentration of the water-insoluble drug is desirably such that the applied amount of the water-insoluble drug in the resulting coating layer can be preferably 0.1 μg/mm² to 10 μg/mm², more preferably 0.5 μg/mm² to 5 μg/mm², further preferably 0.5 μg/mm² to 3.5 μg/mm², and still further preferably 1.0 μg/mm² to 3.0 μg/mm².

(2) Basic Compound Positively Charged at Physiological pH

The physiological pH refers to a pH range in a living body, primarily in blood, specifically a range of preferably pH 6.0 to 8.0, more preferably pH 7.0 to 7.7, and further preferably pH 7.3 to 7.5.

Besides, the disclosed basic compound refers to a Lewis base, which is an electron donor, a Bronsted base, which is a proton acceptor, or a compound which is dissociated into a cation and an anion in an aqueous solution and the aqueous solution of which shows a basic pH.

Examples of the basic compound which is positively charged at physiological pH include a basic compound having an amidino group, a basic compound having a piperidino ring, a basic compound having two or more amino groups in one molecule, a quaternary ammonium cation, and salts thereof.

The amount of the basic compound or compounds positively charged at physiological pH which are contained in the coating composition is not particularly limited, but it is preferable that the amount, in total, is preferably 0.5 to 200 parts by weight, more preferably 4 to 100 parts by weight, and further preferably 6 to 40 parts by weight, based on 100 parts by weight of the water-insoluble drug.

<Basic Compound Having Amidino Group>

A compound having an amidino group represented by the following formula is a strong base, since a protonated conjugate acid is stabilized with positive charges delocalized to the two nitrogen atoms.

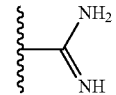

Preferable examples of the basic compound having an amidino group include compounds represented by the following formula (I):

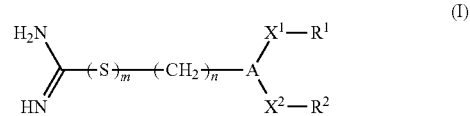

where A is an aromatic ring, $R^1$ and $R^2$ are each independently an alkyl or alkenyl group of 10 to 25 carbon atoms, $X^1$ and $X^2$ are each independently O, S, COO, OCO, CONH or NHCO, m is 0 or 1, and n is 0 or an integer of 1 to 6.

The compounds represented by the formula (I) have a good balance between a hydrophobic moiety (alkyl or alkenyl groups of 10 to 25 carbon atoms) and a hydrophilic moiety (amidino group). Particularly, the hydrophobic moiety enhances affinity for the water-insoluble drug and the balloon surface, whereas the hydrophilic moiety (the positive charges of the amidino group) enhances affinity for negatively charged cell surfaces. This ensures that the durability of the drug coating layer, formed on at least part of a surface of a medical device by use of the disclosed coating composition, during the process of delivery to a target area is enhanced, and the migration of the drug to tissue in the target area is improved.

More preferable examples of the basic compound having an amidino group include compounds represented by the following formula (II):

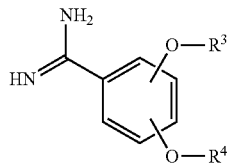

(II)

where $R^3$ and $R^4$ are each independently an alkyl group of 10 to 18 carbon atoms.

The method for preparing the compound represented by the formula (II) is not specifically restricted, and the compound can be prepared, for example, by the method described in PCT Patent Publication No. WO 1997/47166, the content of which is incorporated by reference.

This will be described below by showing an example of the method of preparing dialkyloxybenzamidines.

First, using a dihydroxybenzonitrile (2,3-dihydroxybenzonitrile, 3,4-dihydroxybenzonitrile or 3,5-dihydroxybenzonitrile) and an alkyl halide, a $S_N2$ reaction is conducted in an aprotic solvent such as acetone in the presence of an alkali, to substitute the hydrogen atoms in the hydroxyl groups with alkyl groups, thereby obtaining a dialkyloxybenzonitrile.

Next, the dialkyloxybenzonitrile thus obtained is subjected to a Pinner reaction by adding an alcohol such as methanol in the presence of an acid catalyst such as hydrogen chloride, to obtain a Pinner salt. The Pinner salt thus obtained is subjected to a nucleophilic addition reaction in the presence of ammonia or an amine, to obtain a dialkyloxybenzamidine.

More preferable examples of the basic compound having an amidino group include compounds represented by the following formula (III) or the following formula (IV).

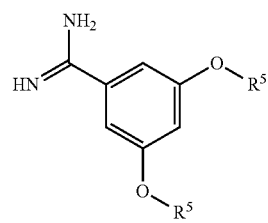

(III)

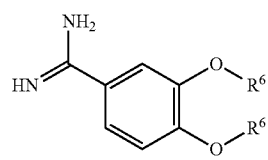

(IV)

Further preferable examples of the basic compound having an amidino group include compounds represented by the following formula (V).

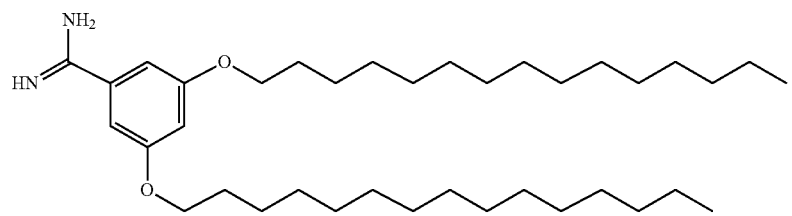

(V)

Examples of salts of the basic compound having an amidino group include: salts formed from a cation formed through acceptance of a proton by the compound having an amidino group and an anion; and salts formed by donation of a lone pair of electrons to a Lewis acid by the compound having an amidino group. Preferable salts include hydrochloride, carbonate, hydrogen carbonate, phosphate, and pyrophosphate.

<Basic Compound Having Piperidine Ring>

A compound having a structure obtained by substitution of a hydrogen atom of piperidine represented by the following formula (a compound having a piperidine ring) behaves as a Lewis base or a Bronsted base, as the nitrogen atom on the piperidine ring has a lone pair of electrons.

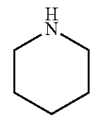

Preferable examples of the basic compound having a piperidine ring include compounds represented by the following formula (VI):

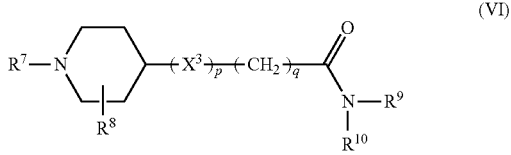

where $R^7$ is a hydrogen atom or an alkyl or alkenyl group of 1 to 8 carbon atoms, $R^8$ is a hydrogen atom or an alkyl or alkenyl group of 1 to 8 carbon atoms, $R^9$ and $R^{10}$ are each independently a hydrogen atom or an alkyl or alkenyl group of 1 to 25 carbon atoms (exclusive of the case where both $R^9$ and $R^{10}$ are hydrogen), $X^3$ is —O— or —S—, p is 0 or 1, and q is 0 or an integer of 1 to 10.

Examples of salts of the basic compound having a piperidine ring include: salts formed from a cation formed by acceptance of a proton by the compound having a piperidine ring and an anion; and salts formed by donation of a lone pair of electrons of the nitrogen atom of the compound having a piperidine ring to a Lewis acid. Preferable salts include hydrochloride, carbonate, hydrogen carbonate, phosphate, and pyrophosphate.

<Basic Compound Having two or more Amino Groups in one Molecule>

Amino groups may each be any of a primary amino group, a secondary amino group and a tertiary amino group, and the combination of two or more amino groups is not restricted in any way. The nitrogen atoms in the amino groups have lone pairs of electrons, and the compound behaves as a Lewis base or a Bronsted base.

Preferable examples of the basic compound having two or more amino groups in one molecule include a compound represented by the following formula (VII).

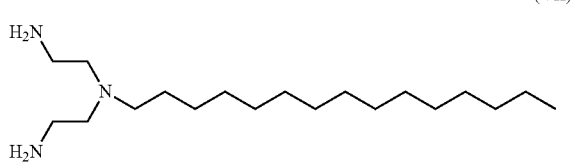

Preferable examples of salts of the basic compound having two or more amino groups in one molecule include: salts formed from a cation formed by acceptance of a proton by the basic compound having two or more amino groups in one molecule and an anion; and salts formed by donation of a lone pair or pairs of electrons of the nitrogen atom or atoms of the basic compound having two or more amino groups in one molecule to a Lewis acid. Preferable salts include hydrochloride, carbonate, hydrogen carbonate, phosphate, and pyrophosphate.

<Quaternary Ammonium Cation>

Preferable examples of the quaternary ammonium cation include those which are represented by the following formula (VIII):

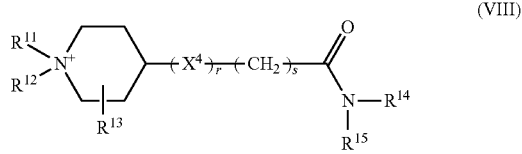

where $R^{11}$ and $R^{12}$ are each independently an alkyl or alkenyl group of 1 to 8 carbon atoms, R13 is a hydrogen atom or an alkyl or alkenyl group of 1 to 8 carbon atoms, $R^{14}$ and $R^{15}$ are each independently a hydrogen atom or an alkyl or alkenyl group of 1 to 25 carbon atoms (exclusive of the case where both $R^{14}$ and $R^{15}$ are hydrogen), $X^4$ is —O— or —S—, r is 0 or 1, and s is 0 or an integer of 1 to 10.

An anion for forming a salt with the quaternary ammonium cation is not specifically restricted. Preferable anions include hydride ion, carbonate ion, hydrogen carbonate ion, phosphate ion, and pyrophosphate ion.

(3) Other Preferable Ingredients

The disclosed coating composition, preferably, further contains a lower alcohol. When the coating composition contains a lower alcohol, the blood vessel penetrating property of the water-insoluble drug can be augmented, and the evenness of the drug coating layer can be enhanced. The lower alcohol is not specifically restricted so long as it is an alcohol of up to 5 carbon atoms, and is preferably a triol or tetraol, more preferably glycerin (also called "glycerol" or "propane-1,2,3-triol"), 1,2,4-butanetriol (also called "butane-1,2,4-triol") or erythritol (also called "(2R,3S)-butane-1,2,3,4-tetraol"), and further preferably glycerin.

Where the lower alcohol is contained in the disclosed composition, the amount of the lower alcohol contained is not particularly limited, and is preferably 5 to 350 parts by weight, more preferably 20 to 250 parts by weight, and further preferably 30 to 100 parts by weight, based on 100 parts of the water-insoluble drug.

(4) Other Ingredients Which can be Contained

In addition to the above-mentioned ingredients, the disclosed coating composition may contain solvent for the following ingredients, such as water, ethanol, acetone, and tetrahydrofuran. Further, the coating composition may contain other additives so long as they do not hamper the desired effects.

2. Drug Coating Layer

The drug coating layer is a layer formed from the disclosed coating composition, and is a layer that contains the water-insoluble drug and the basic compound positively charged at physiological pH. The disclosed drug coating layer has high affinity for a surface of a medical device, and is unsusceptible to peeling or separation during the process of delivery of the medical device. At a target tissue, an interaction between positive charges in the drug coating layer and negative charges on cell surfaces ensures rapid release of the drug and can enhance migration of the drug to the cell tissue.

The disclosed drug coating layer can be formed by coating a surface of a medical device with the disclosed coating composition, followed by drying, but this method is not restrictive.

The amount of the drug contained in the drug coating layer is not particularly limited, and is preferably 0.1 μg/mm² to 10 μg/mm², more preferably 0.5 μg/mm² to 5 μg/mm², further preferably 0.5 μg/mm² to 3.5 μg/mm², and still further preferably 1.0 μg/mm² to 3.0 μg/mm².

3. Drug Eluting Medical Device

A drug eluting medical device has the disclosed drug coating layer formed on its surface either directly or through a pretreatment such as irradiation with an organic solvent or primer, irradiation with UV rays, etc. The medical device is preferably a medical device which can be expanded radially (circumferentially) within a lumen such as a blood vessel, and is more preferably a balloon catheter or a stent.

On at least part of a surface of the drug eluting medical device, there is formed the disclosed drug coating layer which contains the water-insoluble drug and the basic compound positively charged at physiological pH. The drug coating layer is unsusceptible to peeling or separation during the delivery process of the medical device, since the alkyl group hydrophobic moiety of the basic compound enhances affinity for the water-insoluble drug and the medical device surface. Further, since the basic compound is positively charged at physiological pH, it is expected that affinity for negatively charged tissue in a lesion affected area is enhanced, the drug is rapidly eluted at the target tissue, and the migration of the drug to the tissue is enhanced. In the case of a balloon catheter, the drug coating layer is formed on an outer surface of an expandable portion (balloon). Besides, in the case of a stent, the drug coating layer is formed on an outer surface of an expandable portion.

The material constituting the expandable portion of the medical device is preferably a material which has a certain degree of flexibility and a certain degree of rigidity (hardness) such that the expandable portion can be expanded upon delivery of the medical device to a blood vessel, a tissue or the like and the drug can be released from the drug coating layer formed on the surface of the expandable portion. Specifically, the surface of the expandable portion on which to provide the drug coating layer is formed of a resin. The resin constituting the surface of the expandable portion is not particularly limited, and preferable examples of the resin include polyamides. In other words, at least part of the surface of the expandable portion of the medical device which is to be coated with the drug is a polyamide. The polyamides are not specifically restricted so long as they are polymers having amide linkages. Examples of the polyamides include: homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc.; copolymers such as caprolactam/lauryllactam copolymer (nylon 6/12), caprolactam/aminoundecanoic acid copolymer (nylon 6/11), caprolactam/w-aminononanoic acid copolymer (nylon 6/9), caprolactam/hexamethylene diammonium adipate copolymer (nylon 6/66), etc.; and aromatic polyamides such as a copolymer of adipic acid with metaxylenediamine, or a copolymer of hexamethylenediamine with m,p-phthalic acid. Further, polyamide elastomers as block copolymer wherein a hard segment is composed of nylon 6, nylon 66, nylon 11, nylon 12 or the like and a soft segment is composed of polyalkylene glycol, polyether, aliphatic polyester or the like, can also be used as a base material for the disclosed medical device. The polyamides may be used either singly or in combination of two or more of them.

Besides, for the other portions than the expandable portion of the medical device, there can be used, for example, thermoplastic resins such as polyolefins such as polyethylene, polypropylene, ethylene-propylene copolymer, etc., polyesters such as polyethylene phthalate, etc., polyvinyl chloride, ethylene-vinyl acetate copolymer, crosslinked ethylene-vinyl acetate copolymer, polyurethane, etc., polyamides, polyamide elastomers, silicone rubbers, latex rubber, and so on.

4. Treating Method using Drug Eluting Medical Device

A treating method using the disclosed drug eluting medical device includes a step of eluting a drug from a drug coating layer formed on at least part of a surface of the medical device. More particularly, the treating method using the disclosed drug eluting medical device preferably includes: a step of delivering the medical device into a lumen; a step of radially expanding the medical device within the lumen; and a step of eluting a drug from the drug coating layer formed on at least part of the surface of the medical device and permitting the drug to act on the lumen.

The step of delivering the disclosed drug eluting medical device into a lumen can be carried out in the same manner as in the cases of conventionally known balloons and stents. For instance, in the case of delivering a drug eluting balloon or stent to a stenosed part of a coronary artery, a tubular guiding catheter is inserted through an artery at a patient's wrist or femoral region to an inlet portion of the coronary artery of the heart, a guide wire is inserted into the guiding catheter, and the balloon catheter is inserted along the guide wire, whereby the balloon or stent can be delivered to the stenosed part.

The step of radially expanding the disclosed drug eluting medical device within the lumen can be performed in the same manner as in the cases of conventionally known balloons and stents.

The step of eluting the drug from the drug coating layer formed on at least part of the surface of the disclosed drug eluting medical device and allowing the drug to act on the lumen can be carried out by a method wherein the medical device expanded within the lumen is maintained with the drug eluting balloon expanded for a time of several tens of seconds to several minutes or wherein the drug eluting stent is left indwelling. As a result, the lumen is dilated, and the drug in the drug coating layer acts on the tissue of the lumen.

The treating method using the disclosed drug eluting medical device can be applied, for example, to treatment of angiostenosis, and where a drug capable of inhibiting cell growth, such as carcinostatic or immunosuppressant (e.g., paclitaxel), is utilized as the drug, restenosis can be prevented.

The basic compound positively charged at physiological pH which is contained in the disclosed coating composition has high biocompatibility, such as no possibility of inducing thrombosis formation. Therefore, it is possible to provide a drug eluting medical device that is desirable from the viewpoint of safety, as well.

EXAMPLES

The disclosed embodiments will be described in detail below by showing Examples, but the invention is not limited to the following Examples.

[Synthesis of 3,5-dipentadecyloxybenzamidine]

3,5-Dihydroxybenzonitrile in an amount of 0.50 g, 2.70 g of 1-bromopentadecane, 2.56 g of potassium carbonate and 30 ml of acetone were mixed, and the mixture was heated at reflux overnight. Thereafter, water was added to the mixture, and the reaction mixture was subjected to extraction with methylene chloride, washing with water, and then to drying with anhydrous magnesium sulfate. The solvent was distilled away, to obtain 0.33 g of 3,5-dipentadecyloxybenzonitrile as colorless crystal. The 3,5-dipentadecyloxybenzonitrole was dissolved in a mixed solvent of 20 ml of methanol and 35 ml of benzene, and hydrogen chloride gas was introduced into the mixture under ice cooling for one hour. The solvent was distilled away at reduced pressure to obtain a crystal, which was recrystallized from chloroform and hexane, to obtain 0.28 g of 3,5-dipentadecyloxy-α-methoxy-α-iminotoluene hydrochloride. This hydrochloride was dissolved in 10 ml of chloroform, ammonia gas was introduced into the resulting solution under ice cooling for 40 minutes, and then the reaction mixture was heated at reflux for 4.5 hours. The solvent was distilled away at reduced pressure, to obtain a solid, from which chloroform-insoluble matter was removed, to obtain 0.20 g of a colorless crystal. Instrumental analysis data on this colorless crystal supports the structure of the following formula.

$^1$H-NMR (CDCl$_3$) δ (ppm): 6.92 (s, 2H), 6.65 (s, 1H), 3.99 (t, 4H, J=6.4 Hz), 1.77-1.22 (m, 52H), 0.88 (t, 6H, J=6.8 Hz)

Melting point: 149 to 150° C.

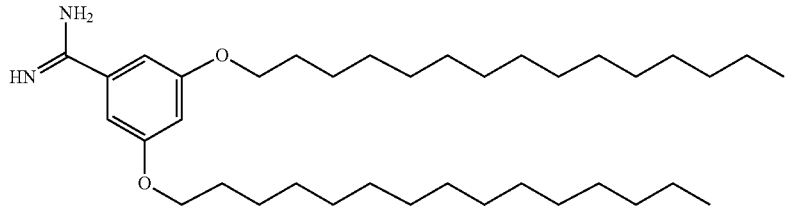 [SMILES: CCCCCCCCCCCCCCCOc1cc(OCCCCCCCCCCCCCCC)cc(C(=N)N)c1]

[Fabrication of Drug Eluting Balloon]

Example 1

(1) Preparation of Coating Solution 1

1.1) 3,5-dipentadecyloxybenzamidine hydrochloride (hereinafter referred to as "TRX-20") (60 mg) synthesized above was weighed and was added to tetrahydrofuran (hereinafter referred to as "THF") (1 mL), to prepare a 60 mg/mL TRX-20/THF solution.

1.2) Paclitaxel (hereinafter referred to as "PTX"; CAS No. 33069-62-4) (80 mg) was weighed and dissolved in THF (2 mL) added thereto, to prepare a 40 mg/mL PTX/THF solution.

1.3) The 60 mg/mL TRX-20/TFH solution (24 μL) and the 40 mg/mL PTX/THF solution (200 μL) were mixed, to prepare a coating solution 1. The mass ratio of TRX-20 to PTX in the coating solution prepared was TRX-20/PTX=0.18/1.

(2) Coating of Balloon with Drug

A balloon catheter (produced by Terumo Corporation, with a balloon portion (expandable portion) formed of nylon; the same applies hereafter) with an expandable portion sized to be 3.0 mm in diameter and 20 mm in length when expanded was prepared. The balloon in an expanded state was coated with the coating solution 1 by use of a pipette so that the amount of paclitaxel would be about 3 μg/mm$^2$, followed by drying the balloon, to fabricate a drug eluting balloon.

Example 2

(1) Preparation of Coating Solution 2

1.1) TRX-20 (60 mg) synthesized above was weighed and was added to and dissolved in THF (1 mL), to prepare a 60 mg/mL TRX-20/THF solution.

1.2) PTX (80 mg) was weighed and dissolved in THF (2 mL) added thereto, to prepare a 40 mg/mL PTX/THF solution.

1.3) The 60 mg/mL TRX-20/THF (48 μL) and the 40 mg/mL PTX/THF solution (200 μL) were mixed, to prepare a coating solution 2. The mass ratio of TRX-20 to PTX in the coating solution prepared was TRX-20/PTX=0.36/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 2 prepared above, a drug eluting balloon was fabricated in the same manner as in Example 1 so that the amount of paclitaxel was about 3 μg/mm$^2$.

Example 3

(1) Preparation of Coating Solution 3

1.1) TRX-20 (40 mg) synthesized above was weighed and was added to and dissolved in THF (1 mL), to prepare a 40 mg/mL TRX-20/THF solution.

1.2) PTX (80 mg) was weighed and dissolved in THF (2 mL) added thereto, to prepare a 40 mg/mL PTX/THF solution.

1.3) The 40 mg/mL TRX-20/THF solution (120 μL) and the 40 mg/mL PTX/THF solution (200 μL) were mixed, to prepare a coating solution 3. The mass ratio of TRX-20 to PTX in the coating solution prepared was TRX-20/PTX=0.6/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 3 prepared above, a drug eluting balloon was fabricated in the same manner as in Example 1 so that the amount of paclitaxel was about 3 μg/mm$^2$.

Example 4

(1) Preparation of Coating Solution 4

1.1) TRX-20 (40 mg) synthesized above was weighed and was added to and dissolved in THF (1 mL), to prepare a 40 mg/mL TRX-20/THF solution.

1.2) PTX (80 mg) was weighed and dissolved in THF (2 mL) added thereto, to prepare a 40 mg/mL PTX/THF solution.

1.3) The 40 mg/mL TRX-20/THF solution (120 μL) and the 40 mg/mL PTX/THF solution (100 μL) were mixed, to prepare a coating solution 4. The mass ratio of TRX-20 to PTX in the coating solution prepared was TRX-20/PTX=1.2/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 4 prepared above, a drug eluting balloon was fabricated in the same manner as in Example 1 so that the amount of paclitaxel was about 3 μg/mm$^2$.

Example 5

(1) Preparation of Coating Solution 5

1.1) TRX-20 (60 mg) synthesized above was weighed and dissolved in THF (1 mL) added thereto, to prepare a 60 mg/mL TRX-20/THF solution.

1.2) PTX (40 mg) was weighed and was added to and dissolved in an anhydrous ethanol/acetone mixed solution composed of anhydrous ethanol (1 mL) and acetone (1 mL), to prepare a 40 mg/mL PTX/EtOH solution.

1.3) The 60 mg/mL TRX-20/THF solution (24 µL) and the 40 mg/mL PTX/EtOH solution (200 µL) were mixed, to prepare a coating solution 5. The mass ratio of TRX-20 to PTX in the coating solution prepared was TRX-20/PTX=0.18/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 5 prepared above, a drug eluting balloon was fabricated in the same manner as in Example 1 so that the amount of paclitaxel was about 3 µg/mm$^2$.

Example 6

(1) Preparation of Coating Solution 6

1.1) TRX-20 synthesized above, in an amount of 60 mg, was weighed and was added to and dissolved in THF (1 mL), to prepare 60 mg/mL TRX-20/THF solution.

1.2) PTX (40 mg) was weighed and was added to and dissolved in an anhydrous ethanol/acetone mixed solution composed of anhydrous ethanol (1 mL) and acetone (1 mL), to prepare a 40 mg/mL PTX/EtOH solution.

1.3) The 60 mg/mL TRX-20/THF solution (48 µL) and the 40 mg/mL PTX/EtOH solution (200 µL) were mixed, to prepare a coating solution 6. The mass ratio of TRX-20 to PTX in the coating solution prepared was TRX-20/PTX=0.36/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 6 prepared above, a drug eluting balloon was fabricated in the same manner as in Example 1 so that the amount of paclitaxel was about 3 µg/mm$^2$.

Example 7

(1) Preparation of Coating Solution 7

1.1) TRX-20 (140 mg) synthesized above was weighed and was added to and dissolved in THF (2 mL), to prepare a 70 mg/mL TRX-20/THF solution.

1.2) PTX (168 mg) was weighed and was added to and dissolved in an anhydrous ethanol/acetone mixed solution composed of anhydrous ethanol (1.5 mL) and acetone (1.5 mL), to prepare a 56 mg/mL PTX/EtOH solution.

1.3) The 70 mg/mL TRX-20/THF solution (30 µL) and the 56 mg/mL PTX/EtOH solution (200 µL) were mixed, to prepare a coating solution 7. The mass ratio of TRX-20 to PTX in the coating solution prepared was TRX-20/PTX=0.19/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 7 prepared as above, a drug eluting balloon was fabricated in the same manner as in Example 1 so that the amount of paclitaxel was about 3 µg/mm$^2$.

Example 8

(1) Preparation of Coating Solution 8

1.1) TRX-20 (140 mg) synthesized above was weighed and was added to and dissolved in THF (2 mL), to prepare a 70 mg/mL TRX-20/THF solution.

1.2) PTX (112 mg) was weighed and was added to and dissolved in TFH (2 mL), to prepare a 56 mg/mL PTX/THF solution.

1.3) Glycerin (CAS No. 56-81-5) (500 µL) and anhydrous ethanol (500 µL) were mixed, to prepare a 50% glycerin solution.

1.4) The 70 mg/mL TRX-20/THF solution (60 µL), the 56 mg/mL PTX/THF solution (200 µL) and the 50% glycerin solution (17 µL) were mixed, to prepare a coating solution 8. The mass ratio of TRX-20 to PTX in the coating solution prepared was TRX-20/PTX=0.38/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 8 prepared, a drug eluting balloon was fabricated in the same manner as in Example 1 so that the amount of paclitaxel was about 3 µg/mm$^2$.

Example 9

(1) Preparation of Coating Solution 9

1.1) TRX-20 (140 mg) synthesized above was weighed and was added to and dissolved in THF (2 mL), to prepare a 70 mg/mL TRX-20/THF solution.

1.2) PTX (112 mg) was weighed and was added to and dissolved in an anhydrous ethanol/acetone (1/1) mixed solution, to prepare a 56 mg/mL PTX/EtOH solution.

1.3) Glycerin (500 µL) and anhydrous ethanol (500 µm) were mixed, to prepare a 50% glycerin solution.

1.4) The 70 mg/mL TRX-20/THF solution (11 µL), the 56 mg/mL PTX/EtOH solution (200 µL), and the 50% glycerin solution (6 µL) were mixed, to prepare a coating solution 9. The mass ratio of TRX-20 to PTX in the coating solution prepared was TRX-20/PTX=0.07/1.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 9 prepared, a drug eluting balloon was fabricated in the same manner as in Example 1 so that the amount of paclitaxel was about 3 µg/mm$^2$.

Example 10

(1) Preparation of Coating Solution 10

1.1) TRX-20 (140 mg) synthesized above was weighed and was added to and dissolved in THF (2 mL), to prepare a 70 mg/mL TRX-20/THF solution.

1.2) PTX (112 mg) was weighed and was added to and dissolved in an anhydrous ethanol/acetone (1/1) mixed solution, to prepare a 56 mg/mL PTX/EtOH solution.

1.3) Glycerin (1,000 μL) and anhydrous ethanol (1,000 μL) were mixed, to prepare a 50% glycerin solution.

1.4) The 70 mg/mL TRX-20/THF solution (30 μL), the 56 mg/mL PTX/EtOH solution (200 μL), the 50% glycerin solution (15 μL), and anhydrous ethanol (100 μL) were mixed, to prepare a coating solution 10. The mass ratio of TRX-20 to PTX in the coating solution prepared was TRX-20/PTX=0.19/1.

(2) Coating of Balloon with Drug

A balloon catheter (produced by Terumo Corporation, with a balloon portion (expandable portion) formed of nylon) with an expandable portion sized to be 2.0 mm in diameter and 20 mm in length when expanded was prepared. Using the coating solution 10 prepared above, a drug eluting balloon was fabricated in the same manner as in Example 1 so that the amount of paclitaxel was about 3 μg/mm².

Example 11

(1) Preparation of Coating Solution 11

1.1) TRX-20 (140 mg) synthesized above was weighed and was added to and dissolved in THF (2 mL), to prepare a 70 mg/mL TRX-20/THF solution.

1.2) PTX (112 mg) was weighed and was added to and dissolved in an anhydrous ethanol/acetone (1/1) mixed solution, to prepare a 56 mg/mL PTX/EtOH solution.

1.3) Glycerin (1,000 μL) and an anhydrous ethanol (1,000 μL) were mixed, to prepare a 50% glycerin solution.

1.4) The 70 mg/mL TRX-20/THF solution (11 μL), the 56 mg/mL PTX/EtOH solution (200 μL), and the 50% glycerin solution (6 μL) were mixed, to prepare a coating solution 11. The mass ratio of TRX-20 to PTX in the coating solution prepared was TRX-20/PTX=0.07.

(2) Coating of Balloon with Drug

A balloon catheter (produced by Terumo Corporation, with a balloon portion (expandable portion) formed of nylon) with an expandable portion sized to be 2.0 mm in diameter and 20 mm in length when expanded was prepared. Using the coating solution 11 prepared above, a drug eluting balloon was fabricated in the same manner as in Example 1 so that the amount of paclitaxel was about 3 μg/mm².

Comparative Example C1

(1) Preparation of Coating Solution 12

1.1) Hydrogenated soybean phospholipid (phosphatidylcholine, HSPC) (SPC-3, Lipoid GmbH, molecular weight: 790) (100 mg) was weighed, and dissolved in anhydrous ethanol (2 mL), to prepare a 50 mg/mL hydrogenated soybean phospholipid solution.

1.2) Sodium acetylhyaluronate (AcHA, average molecular weight=100,000; degree of substitution with acetyl group=2.6 to 3.8/unit; CAS No. 287390-12-9) (5 mg) was weighed, and was added to and mixed with an anhydrous ethanol/water mixture composed of anhydrous ethanol (0.8 mL) an RO water (0.2 mL), to prepare a 0.5% acetylhyaluronic acid solution.

1.3) PTX (80 mg) was weighed and was added to and dissolved in an anhydrous ethanol/acetone mixed solution composed of anhydrous ethanol (1 mL) and acetone (1 mL), to prepare a 40 mg/mL paclitaxel solution.

1.4) The 50 mg/mL hydrogenated soybean phospholipid solution (40 μL), the 0.5% acetylhyaluronic acid solution (40 μL), anhydrous ethanol (120 μL), and the 40 mg/mL paclitaxel solution (200 μL) were mixed, to prepare a coating solution 13.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 12 prepared above, a drug eluting balloon was fabricated in the same manner as in Example 1 so that the amount of paclitaxel was about 3 μg/mm².

Comparative Example C2

(1) Preparation of Coating Solution 13

1.1) An ethyl acrylate (EA)-methyl methacrylate (MMA) copolymer dispersion (Eudragit NE30D, Higuchi Inc.) (200 μL) was weighed, and anhydrous ethanol (1,800 μL) was added thereto, to prepare a 10% ethyl acrylate-methyl methacrylate copolymer solution.

1.2) PTX (80 mg) was weighed and was added to and dissolved in an anhydrous ethanol/acetone (1/1) mixed solution, to prepare a 40 mg/mL PTX/EtOH solution.

1.3) The 10% ethyl acrylate-methyl methacrylate copolymer solution (20 μL) and the 40 mg/mL PTX/EtOH solution (200 μL) were mixed, to prepare a coating solution 10.

(2) Coating of Balloon with Drug

A balloon catheter (produced by Terumo Corporation, with a balloon portion (expandable portion) formed of nylon) with an expandable portion sized to be 3.0 mm in diameter and 20 mm in length when expanded was prepared. Using the coating solution 13 prepared above, a drug eluting balloon was fabricated in the same manner as in Example 1 so that the amount of paclitaxel was about 3 μg/mm².

Comparative Example C3

Commercially available drug-eluting balloons In. Pact (produced by Invatec S.p.A.; expandable portion: 3.0 mm in diameter, 20 mm in length) were prepared.

[Evaluation of Drug Coating Layer Durability Using Mimic Blood Vessel]

In order to evaluate how much the drug coating layer is separated in the process of delivery to a lesion affected area, for the drug releasing balloons in Examples 1 to 6 and Comparative Examples C1 and C2, a drug coating layer durability test was carried out by performing a delivering operation using a mimic blood vessel and determining the amount of paclitaxel remaining on the balloon after the delivery. Note that the drug coating layer durability test was conducted by the following procedure.

(1) A hollow mimic blood vessel 1 with a 90-degree angle was prepared, and a guiding catheter 2 (outside diameter: 5 Fr) was inserted and passed in the mimic blood vessel 1 (see FIG. 1).

(2) The inside of the guiding catheter 2 was filled with phosphate-buffered saline (PBS) warmed at 37° C.

(3) The drug releasing balloon fabricated (with expandable portion sized 3.0 mm in diameter and 20 mm in length when expanded) was folded by use of a wrapping machine.

(4) The balloon 4 after wrapping was inserted into the guiding catheter filled with the PBS, and a delivering operation of delivering the balloon toward an outlet of the guiding catheter was performed for one minute.

(5) The balloon having been delivered in the guiding catheter was recovered, and the amount of paclitaxel remaining on the balloon was determined by liquid chromatography. Further, the remaining rate of paclitaxel was calculated.

The mass rate of paclitaxel remaining on the balloon, per each balloon, after the delivery operation to the amount of paclitaxel per balloon before delivery is given under "Remaining rate of PTX on a balloon after the delivery operation [mass %]" in Table 1. Note that in Table 1, "TRX-20/PTX" means the mass rate of TRX-20 (3,5-dipentadecyloxybenzamidine hydrochloride) to paclitaxel (PTX); "HSPC/AcHA" means the mass ratio of hydrogenated soybean phospholipid (phosphatidylcholine, HSPC) to acetylhyaluronic acid (AcHA); and "EA/MMA" means the mass ratio of ethyl acrylate (EA) ingredient to methyl methacrylate (MMA) ingredient in the ethyl acrylate-methyl methacrylate copolymer.

Figure 2:
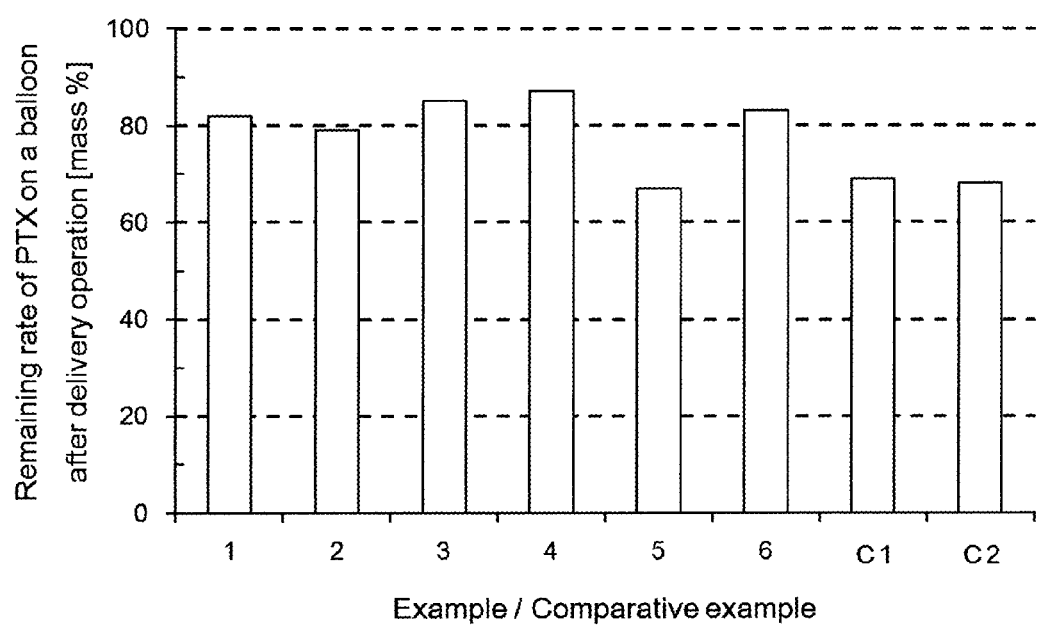
FIG. 2 is a graph representing the remaining rate of paclitaxel on a balloon after a delivery operation, for Examples 1 to 6 and Comparative Examples C1 and C2, in the drug coating layer durability evaluation using a mimic blood vessel.

In addition, FIG. 2 shows a graph representing the remaining rate of paclitaxel on a balloon after the delivery operation for Examples 1 to 6 and Comparative Examples C1 and C2 in the drug coating layer durability evaluation using the mimic blood vessel. In FIG. 2, the axis of abscissas represents Examples or Comparative Examples, wherein numerals 1 to 6 mean Examples 1 to 6, respectively, and alphabet-accompanied numerals C1 and C2 mean Comparative Examples C1 and C2, respectively. Besides, the axis of ordinates represents the remaining rate (mass %) of paclitaxel on a balloon after the delivery operation. The "mass %" means "% by mass."

Figure 3:
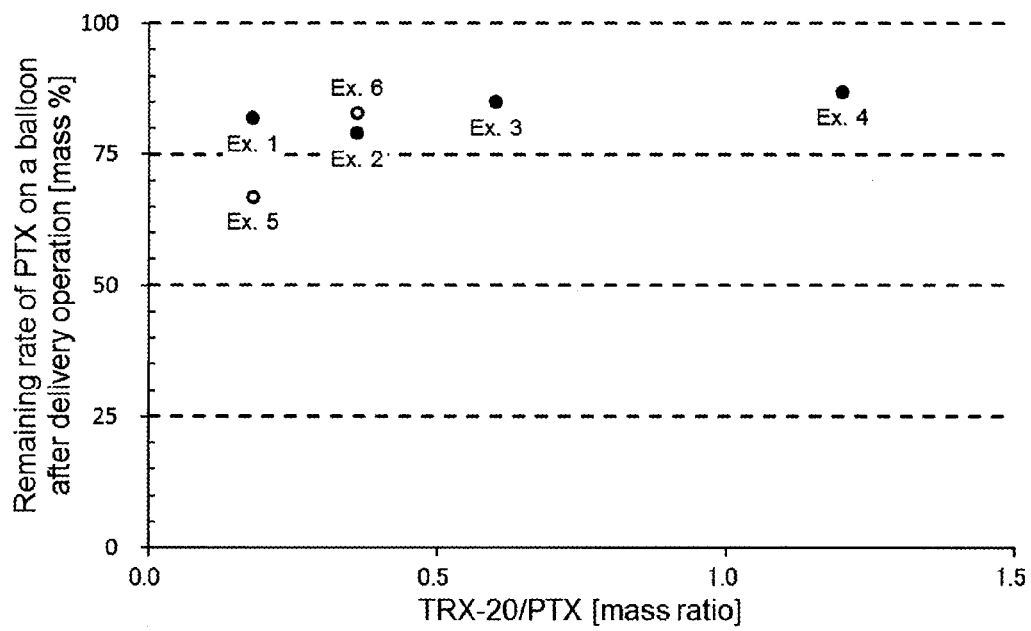
FIG. 3 is a graph representing the relation between mass ratio of TRX-20 to paclitaxel and the remaining rate of paclitaxel on a balloon, for Examples 1 to 6, in the drug coating layer durability evaluation using a mimic blood vessel.

Further, FIG. 3 shows a graph representing the relation between the mass ratio of TRX-20 to paclitaxel and the remaining rate of paclitaxel on a balloon, for Examples 1 to 6, in the drug coating layer durability evaluation using the mimic blood vessel. In FIG. 3, the axis of abscissas represents the mass ratio (TRX-20/PTX) of TRX-20 to paclitaxel (PTX), wherein "mass ratio" means "ratio by mass." Besides, the axis of ordinates represents the remaining rate of paclitaxel on a balloon after the delivery operation (mass %), wherein "mass %" means "% by mass." Note that the label "Ex." affixed to each plot on the graph means "Example," and Ex. 1 to Ex. 6 means Example 1 to Example 6, respectively.

TABLE 1

| Example/ Comparative example | Coating solution No. | TRX-20/PTX [mass ratio] | Remaining rate of PTX on a balloon after delivery operation [mass %] |
|---|---|---|---|
| 1 | 1 | 0.18/1 | 82 |
| 2 | 2 | 0.36/1 | 79 |
| 3 | 3 | 0.6/1 | 85 |
| 4 | 4 | 1.2/1 | 87 |
| 5 | 5 | 0.18/1 | 67 |
| 6 | 6 | 0.36/1 | 83 |
| C1 | 12 | (HSPC/AcHA) | 69 |
| C2 | 13 | (EA/MMA) | 68 |

From the results shown in Table 1 and FIG. 2, it is seen that in all Examples the remaining rate of PTX on a balloon after the delivery operation was not less than 50 mass %, which shows good durability of the drug coating layer during delivery process. On the other hand, in Comparative Examples C1 and C2, also, the durability of the drug coating layer during the delivery operation was comparatively good.

In addition, from the results shown in FIG. 3, it is seen that the remaining rate of PTX showed little variation with the TRX-20/PTX mass ratio, and that the durability of the drug coating layer during the delivery operation is good at any TRX-20/PTX mass ratio.

[Evaluation of the Durability of the Drug Coating Layer During the Delivery Process]

In order to evaluate how much the drug coating layer is separated in the process of delivery to a lesion affected area, for the drug releasing balloons in Examples 7 to 9, a drug coating layer durability test was carried out by performing a delivery operation using a mimic blood vessel and determining the amount of paclitaxel remaining on the balloon after the delivery. Note that the drug coating layer durability test was conducted by the following procedure.

(1) A hollow mimic blood vessel 1 with a 90-degree angle was prepared, and a guiding catheter 2 (outside diameter: 5 Fr) was inserted and passed in the mimic blood vessel 1 (see FIG. 1).

(2) The inside of the guiding catheter 2 was filled with PBS warmed at 37° C.

(3) The drug releasing balloon catheter 3 fabricated (with expandable portion sized 3.0 mm in diameter and 20 mm in length when expanded) was folded by use of a wrapping machine.

(4) The balloon 4 after wrapping was inserted into the guiding catheter filled with the PBS, and a delivering operation of delivering the balloon toward an outlet of the guiding catheter was performed for one minute.

(5) The balloon having been delivered in the guiding catheter was recovered, and the amount of paclitaxel remaining on the balloon was determined by liquid chromatography. Further, the remaining rate of paclitaxel was calculated.

The mass rate of paclitaxel remaining on a balloon after wrapping based on the amount of paclitaxel per each balloon before wrapping is given under "Remaining rate of PTX on a balloon—after wrapping [mass %]" in Table 2, and the mass proportion of paclitaxel remaining on a balloon after wrapping and the delivery operation based on the amount of paclitaxel per each balloon before wrapping is given under "Remaining rate of PTX on a balloon—after the delivery operation [mass %]" in Table 2. Note that in Table 2, "TRX-20/PTX" means the mass ratio of TRX-20 (3,5-dipentadecyloxybenzamidine hydrochloride) to paclitaxel (PTX).

Figure 4:
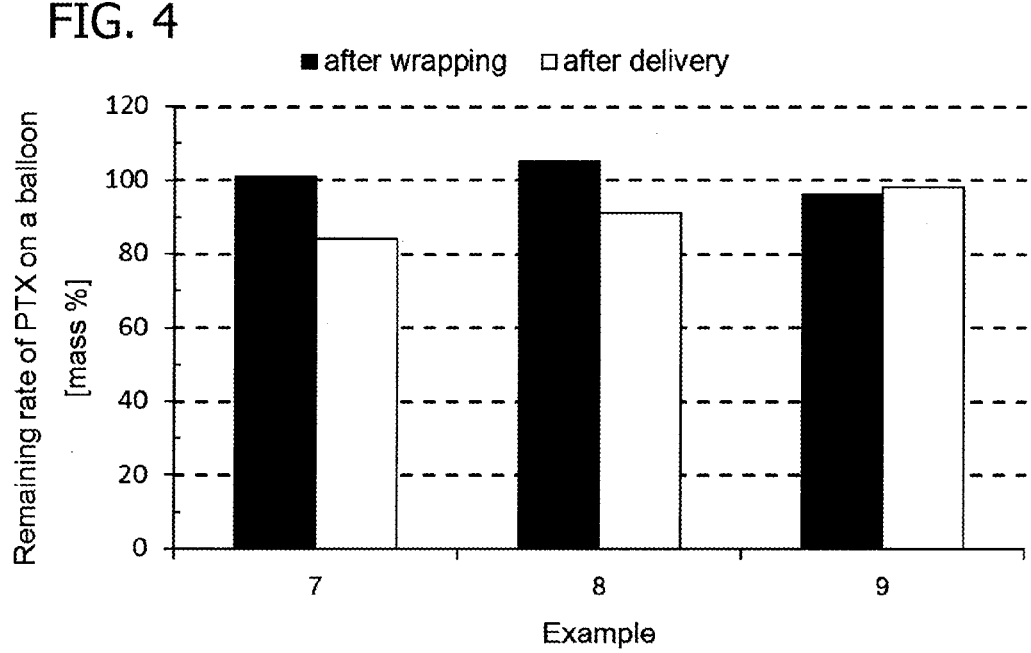
FIG. 4 is a graph representing the remaining rate of paclitaxel on a balloon after wrapping and after a delivery operation, for Examples 7 to 9, in the drug coating layer durability evaluation during the delivery process.

Furthermore, FIG. 4 shows a graph representing the remaining rate of paclitaxel on a balloon after wrapping and after the delivery operation, for Examples 7 to 9, in the evaluation of durability of drug coating layer during delivery process. In FIG. 4, the axis of abscissas represents Examples, and numerals 7 to 9 mean Examples 7 to 9, respectively. Besides, the axis of ordinates represents the remaining rate (mass %) of paclitaxel on a balloon after wrapping or after the delivery operation. In each Example, the left-side bar graph represents the remaining rate of paclitaxel on a balloon immediately after wrapping, while the right-side bar graph represents the remaining rate of paclitaxel on a balloon after wrapping and the delivery operation. In addition, "mass %" means "% by mass."

TABLE 2

| | Coating solution | | Remaining rate of PTX on a balloon | |
|---|---|---|---|---|
| Example | No. | Glycerin [mass %] | TRX-20/ PTX [mass ratio] | after wrapping [mass %] | after delivery operation [mass %] |
| 7 | 7 | 0 | 0.19 | 101 | 84 |
| 8 | 8 | 3 | 0.38 | 105 | 91 |
| 9 | 9 | 1.5 | 0.07 | 96 | 98 |

From the results shown in Table 2 and FIG. 4, it is seen that the durability of the drug coating layer during delivery process was good, both in the case where glycerin was not added to the coating solution (Example 7) and in the cases where glycerin was added to the coating solution (Examples 8 and 9).

[Evaluation of the Migration of Drug to Tissue in Rabbit Iliac Artery]

1. While using the fabricated drug-eluting balloons (Examples 2 and 6, and Comparative Examples C1 and C2) and the commercialized drug-eluting balloon In. Pact (produced by Invatec S.p.A.) (Comparative Example C3), the migration of paclitaxel to vascular tissue in a rabbit iliac artery after one hour from balloon expansion was evaluated by the following procedure.

(1) A guide wire was inserted into a right iliac artery or a left iliac artery of a rabbit under radioscopic observation. Next, the drug eluting balloon (having an expandable portion sized to be 3.0 mm in diameter and 20 mm in length when expanded) was transferred along the guide wire to the iliac artery.

(2) The balloon was expanded at 7 atm for one minute. Immediately thereafter, the balloon was pulled out.

(3) After 60 minutes from the expansion of the balloon, a blood vessel (a range of about 3.5 cm from branching) was sampled.

(4) Methanol was added to the sampled blood vessel, followed by homogenization, to obtain a tissue homogenate.

(5) The tissue homogenate was analyzed by high performance liquid chromatography, to determine the amount of paclitaxel contained in the tissue (the amount of paclitaxel per 1 g of tissue). Furthermore, from the amount of paclitaxel in the coating on the drug eluting balloon and the amount of paclitaxel in the tissue, the migration rate of paclitaxel to vascular tissue (mass rate) was calculated, and, from the amount of paclitaxel remaining on the balloon, the remaining rate (mass rate) was calculated.

The amount of paclitaxel in the tissue is set forth in the column of "Amount of PTX in tissue [µg/g tissue]" in Table 3, the migration rate of paclitaxel to vascular tissue is set forth in the column of "Migration rate of PTX to tissue [mass %]" in Table 3, and the remaining rate of paclitaxel on a balloon is set forth in the column of "Remaining rate of PTX on a balloon [mass %]" in Table 3. Note that in Table 3, "TRX-20/PTX" means the mass ratio of TRX-20 (3,5-dipentadecyloxybenzamidine hydrochloride) to paclitaxel (PTX), "HSPC/AcHA" means the mass ratio of hydrogenated soybean phospholipid (phosphatidylcholine, HSPC) to acetylhyaluronic acid (AcHA), and "EA/MMA" means the mass ratio of the ethyl acrylate (EA) ingredient to the methyl methacrylate (MMA) ingredient in the ethyl acrylate-methyl methacrylate copolymer.

Figure 5:
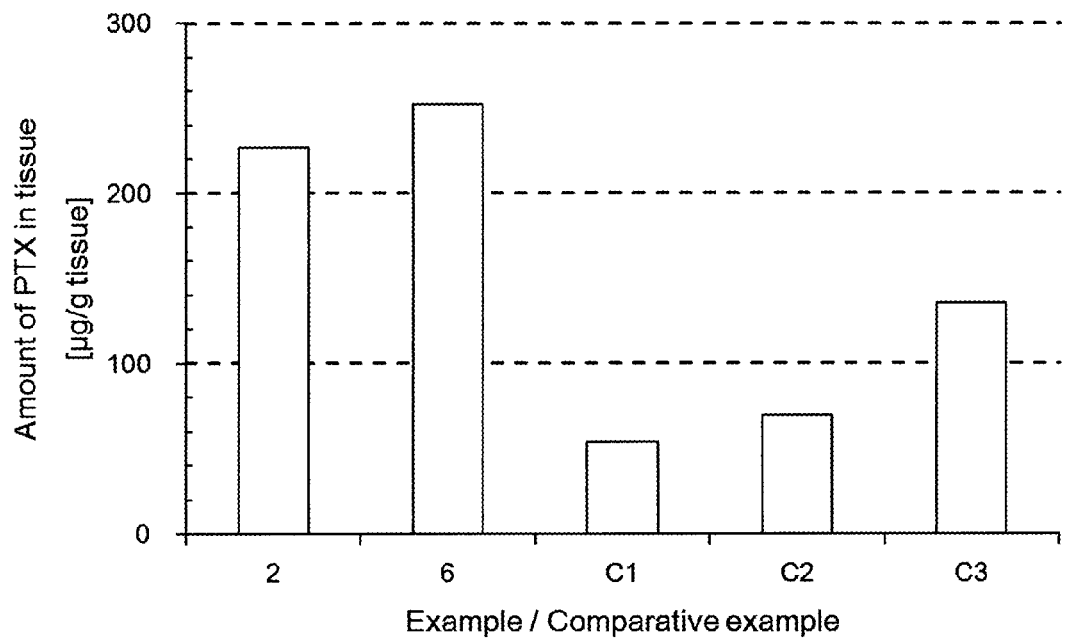
FIG. 5 is a graph representing the amount of paclitaxel in target tissue, for Examples 2 and 6 and Comparative Examples C1 to C3, in evaluation of migration of drug to the tissue in a rabbit iliac artery.

Further, FIG. 5 shows a graph representing the amount of paclitaxel in vascular tissue, for Examples 2 and 6 and Comparative Examples C1 to C3, in the evaluation of the migration of drug to tissue in rabbit iliac artery. In FIG. 5, the axis of abscissas represents Example or Comparative Example, wherein numerals 2 and 6 mean Example 2 and Example 6, respectively. In addition, the axis of ordinates represents the amount of paclitaxel in vascular tissue (µg/g tissue). Besides, "µg/g tissue" means "µg/g tissue."

TABLE 3

| Example/Comparative example | No. | Coating solution TRX-20/PTX [mass ratio] | Amount of PTX in tissue [µg/g tissue] | Migration rate of PTX to tissue [mass %] | Remaining rate of PTX on a balloon [mass %] |
|---|---|---|---|---|---|
| 2 | 2 | 0.36 | 226.5 | 0.9 | 48.7 |
| 6 | 6 | 0.36 | 252.3 | 1.3 | 41.8 |
| C1 | 12 | HSPC/AcHA | 53.6 | 0.2 | 11.8 |
| C2 | 13 | EA/MMA | 69.8 | 0.5 | 27.8 |
| C3 |  | (In.Pact) | 135.4 | 0.6 | 19.4 |

From the results shown in Table 3 and FIG. 5, it is seen that the drug eluting balloons fabricated in Example 2 and Example 6 exhibited remarkable enhancement in the amount of paclitaxel in the tissue and better migration of drug to tissue, as compared to Comparative Examples C1 to C3. Besides, in Examples 2 and 6 it was found that both in the case where THF was used as solvent for PTX (Example 2) and in the case where EtOH/acetone mixed liquid was used as solvent for PTX (Example 6), good migration of drug to tissue could be obtained without being influenced by the solvent.

In addition, in Comparative Example C1 and Comparative Example C2, although the durability of drug coating layer evaluated using the mimic blood vessel was good, the amount of drug that migrated to the tissue was small, which is considered to indicate poor affinity for the target tissue.

Further, in order to indicate the proportion of paclitaxel released into the blood, this proportion was calculated by a method wherein the sum of the proportion of paclitaxel that migrated to the tissue and the proportion of paclitaxel remaining on a balloon is subtracted from 100. The proportion of paclitaxel released into the blood is set forth in the column of "Rate of PTX released into plasma [mass %]" in Table 4. Note that in Table 4, "TRX-20/PTX" means the mass ratio of TRX-20 (3,5-dipentadecyloxybenzamidine hydrochloride) to paclitaxel (PTX).

Figure 6:
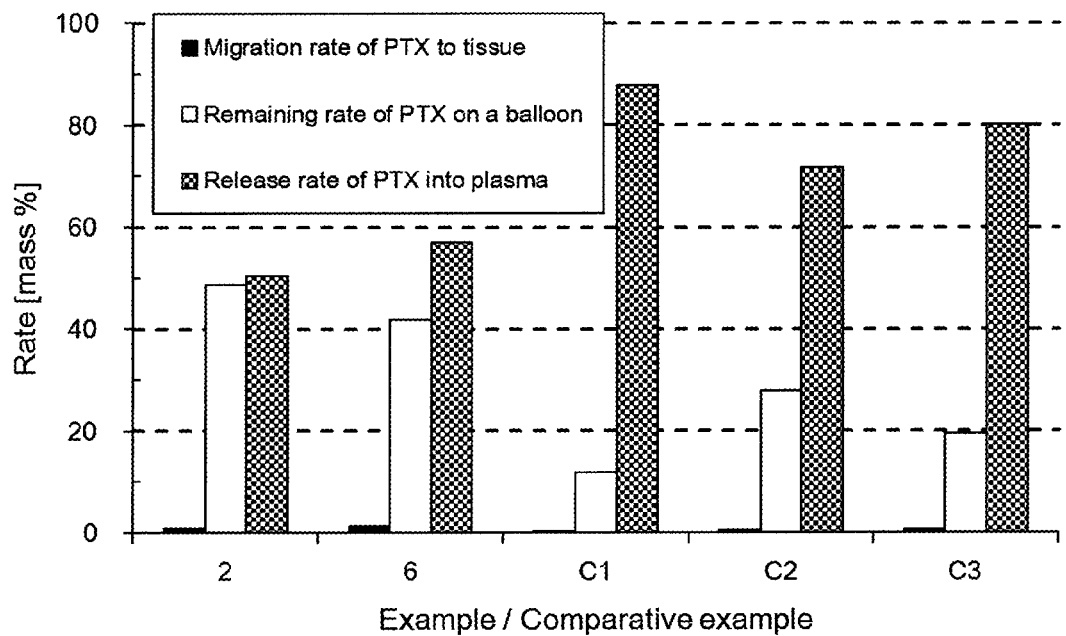
FIG. 6 is a graph representing the migration rate of paclitaxel to vascular tissue, the remaining rate of paclitaxel on a balloon, and the release rate of paclitaxel into plasma, determined on the basis of the results obtained in the evaluation of the migration of drug to the tissue in a rabbit iliac artery.

Furthermore, FIG. 6 shows a graph representing the migration rate of paclitaxel to vascular tissue, the remaining rate of paclitaxel on a balloon, and the rate of paclitaxel released into the blood, which were determined on the basis of the results obtained in the evaluation of migration of drug to tissue in the rabbit iliac artery. In FIG. 6, the axis of abscissas represents Example or Comparative Example, wherein numerals 2 and 6 mean Example 2 and Example 6, respectively, and C1 to C3 means Comparative Examples C1 to C3, respectively. In addition, the axis of ordinates represents migration rate of paclitaxel to vascular tissue (mass %), the remaining rate of paclitaxel on a balloon (mass %), or the release rate of paclitaxel into blood (mass %). In each of Examples and Comparative Examples, the left-side bar graph represents the migration rate of paclitaxel to vascular tissue, the middle bar graph represents the remaining rate of paclitaxel on a balloon, and the right-side bar graph represents the release rate of paclitaxel into blood. Besides, "mass %" means "% by mass."

TABLE 4

| Example/ Comparative example | No. | Coating solution TRX-20/PTX [mass ratio] | Migration rate of PTX to tissue [mass %] | Remaining rate of PTX on a balloon [mass %] | Rate of PTX released into plasma [mass %] |
|---|---|---|---|---|---|
| 2 | 2 | 0.36 | 0.9 | 48.7 | 50.4 |
| 6 | 6 | 0.36 | 1.3 | 41.8 | 56.9 |
| C1 | 12 | HSPC/AcHA | 0.2 | 11.8 | 87.9 |
| C2 | 13 | EA/MMA | 0.5 | 27.8 | 71.7 |
| C3 |  | (IN.PACT) | 0.6 | 19.4 | 80.1 |

From the results shown in Table 4 and FIG. 6, it is seen that the drug eluting balloons fabricated in Example 2 and Example 6 were at least two times higher in the amount of paclitaxel remaining on a balloon, although they were at least two times higher in the migration rate of drug to tissue, as compared to Comparative Examples C1 to C3. From this fact it was made clear that Examples 2 and 6 released less paclitaxel into blood, as compared to Comparative Examples C1 to C3. From the foregoing, it was verified that in Example 2 and Example 6, the drug was efficiently released at the target tissue, most of the paclitaxel which did not migrate to the tissue was recovered in the state of remaining on the balloon, and the amount of paclitaxel released into the blood was suppressed, which is very favorable from the viewpoint of safety. On the other hand, in Comparative Examples C1 to C3, at least 70% of the paclitaxel supported on the balloon was released into the blood, which is unfavorable from the viewpoint of safety.

[Evaluation of Retentivity of Drug in Tissue in Rabbit Iliac Artery at Different Balloon Sizes]

In Examples 10 and 11, using a balloon sized to be 2.0 mm in diameter and 20 mm in length when expanded, smaller in expanded-state diameter than the balloon used in Examples 2 and 6 and Comparative Examples C1 and 2, evaluation of retentivity of drug in tissue in rabbit iliac artery was conducted.

The amount of paclitaxel in the tissue is set forth in the column of "Amount of PTX in tissue [μg/g tissue]" in Table 5, and the remaining rate of paclitaxel on a balloon is set forth in the column "Remaining rate of PTX on a balloon [mass %]" in Table 5. Note that in Table 5, "TRX-20/PTX" means mass ratio of TRX-20 (3,5-dipentadecyloxybenzamidine hydrochloride) to paclitaxel (PTX), and "1H" and "24H" mean after one hour and 24 hours from intravascular expansion, respectively.

Figure 7:
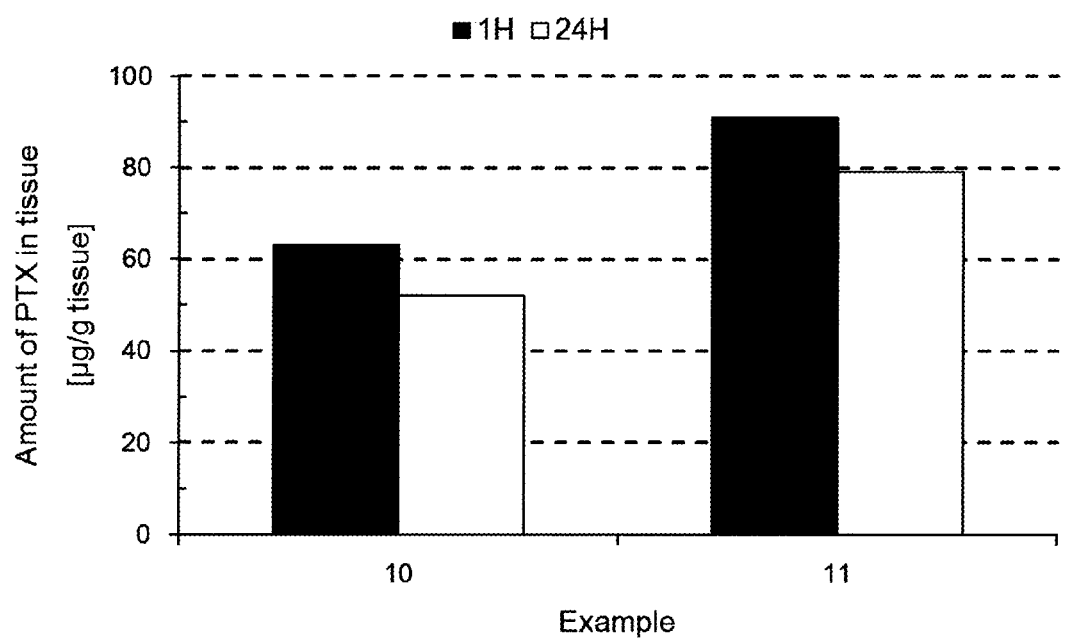
FIG. 7 is a graph representing the amount of paclitaxel in vascular tissue after one hour and after 24 hours from balloon expansion, for Example 10 and Example 11, in the evaluation of retentivity of drug in tissue in a rabbit iliac artery at different balloon sizes.

Further, FIG. 7 shows a graph representing the amount of paclitaxel in the vascular tissue after one hour and after 24 hours from balloon expansion, for Example 10 and Example 11 in the evaluation of retentivity of drug in tissue in a rabbit iliac artery at different balloon sizes. In FIG. 7, the axis of abscissas represents Examples, where numerals 10 and 11 mean Example 10 and Example 11, respectively. In addition, the axis of ordinates represents the amount of paclitaxel in vascular tissue (μg/g tissue). In each Example, the left-side bar graph represents the amount of paclitaxel in the vascular tissue after one hour from balloon expansion, whereas the right-side bar graph represents the amount of paclitaxel in the vascular tissue after 24 hours from balloon expansion. Besides, "μg/g tissue" means "μg/g tissue."

TABLE 5

| | | Coating solution | | Amount of PTX in tissue [μg/g tissue] | | Remaining rate of PTX on a balloon [mass %] |
|---|---|---|---|---|---|---|
| Example | No. | Glycerin [mass %] | TRX-20/PTX [mass ratio] | 1 H | 24 H | |
| 10 | 10 | 3.1 | 0.19 | 63 | 52 | 34 |
| 11 | 11 | 1.5 | 0.07 | 91 | 79 | 23 |

As shown in Table 5, the amounts of paclitaxel of drug in the tissue, recovered after one hour from blood vessel dilation in Examples 10 and 11, were 63 μg/g tissue and 91 μg/g tissue. Thus, the migration of the drug to the tissue could be confirmed, although the amount values were lower as compared to the cases where a balloon sized to be 3.0 mm in diameter when expanded was used (Examples 2 and 6).

Besides, in both of Examples 10 and 11, the amount of paclitaxel in the tissue after one hour from the blood vessel dilation and that after 24 hours from the blood vessel dilation were comparable to each other. This suggests that the amount of paclitaxel having migrated to the vascular tissue does not largely attenuate with time. From this it was made clear that the disclosed drug coating layer ensures that after the migration of the drug to the tissue, a sufficient amount of the drug is retained in the tissue for a long period of time.

When a medical device, for example, a balloon catheter, coated with the disclosed coating composition is used, a drug can be efficiently delivered to a lesion affected area while inhibiting separation of the drug coating layer during the process of delivery to the lesion affected area. In addition, it is possible to promote rapid drug release and migration to tissue from the medical device in the lesion affected area, and to enhance the migration of the drug to the tissue.

The detailed description above describes a coating composition for a drug eluting medical device, a drug coating layer for a drug eluting medical device, a drug eluting medical device coated with the coating composition and a treating method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

DESCRIPTION OF REFERENCE SYMBOLS

1 Mimic blood vessel
2 Guiding Catheter

3 Balloon Catheter
4 Balloon

What is claimed is:

1. A coating composition to be used for a drug-eluting medical device, the coating composition containing paclitaxel and 3,5-dipentadecyloxybenzamidine and/or a salt thereof, wherein the mass ratio of the 3,5-dipentadecyloxybenzamidine and/or a salt thereof to the paclitaxel is 0.36.

2. The coating composition according to claim 1, further containing a lower alcohol.

3. The coating composition according to claim 2, wherein the lower alcohol is glycerin.

4. The coating composition according to claim 1, wherein the medical device is a medical device which can be expanded in a radial direction within a lumen.

5. The coating composition according to claim 4, wherein the medical device is a balloon or a catheter.

6. A drug coating layer formed, by use of the coating composition according to claim 1, on at least part of a surface of the medical device.

7. A medical device provided with the drug coating layer according to claim 6.

8. A treating method comprising:
 delivering the medical device according to claim 7 into a lumen;
 radially expanding the medical device within the lumen; and
  eluting a drug from the drug coating layer formed on at least part of the surface of the medical device and permitting the drug to act on the lumen.

* * * * *